United States Patent [19]

Kurokawa et al.

[11] 4,158,359
[45] Jun. 19, 1979

[54] DEVICE FOR TESTING INFLUENCE OF MEDICINAL OR COSMETIC SUBSTANCE ON SKIN

[75] Inventors: Masahiro Kurokawa; Hisao Iwamoto, both of Odawara, Japan

[73] Assignee: Kanebo Limited, Tokyo, Japan

[21] Appl. No.: 870,922

[22] Filed: Jan. 19, 1978

[30] Foreign Application Priority Data

Jan. 24, 1977 [JP] Japan .................. 52-006243[U]
Dec. 28, 1977 [JP] Japan .................. 52-175958[U]

[51] Int. Cl.² ............................................. A61B 10/00
[52] U.S. Cl. .................................... 128/630; 128/743
[58] Field of Search ............. 128/2 W, 2 R, 2 A, 155, 128/156

[56] References Cited

U.S. PATENT DOCUMENTS

| 2,235,436 | 3/1941 | Laub | 128/2 W |
|---|---|---|---|
| 2,304,817 | 12/1942 | Grozin | 128/2 W |
| 2,969,057 | 1/1961 | Simmons | 128/2 W |
| 3,212,495 | 10/1965 | Osburn et al. | 128/2 W |
| 3,894,531 | 7/1975 | Saunders | 128/2 W |
| 3,965,888 | 6/1976 | Bender | 128/2 W |

*Primary Examiner*—George J. Marlo
*Attorney, Agent, or Firm*—Burgess, Ryan and Wayne

[57] ABSTRACT

Disclosed is a device for accurately testing the influence of a medicinal or cosmetic substance on human or animal skin. The device comprises: a tray having an inside space for containing a medicinal or cosmetic substance to be tested, defined by a bottom and a peripheral side wall, the tray being also provided with a sealing member extending laterally from the top end of the side wall toward the inside and/or the outside of the tray; a porous protecting sheet having one or more holes each capable of containing therein one tray, and; a covering sheet for fixing the tray engaged with the protecting sheet on the skin, having an adhesive surface coated with a pressure-sensitive adhesive agent.

10 Claims, 9 Drawing Figures

DEVICE FOR TESTING INFLUENCE OF MEDICINAL OR COSMETIC SUBSTANCE ON SKIN

The present invention relates to a device for testing the influence of a medicinal or cosmetic substance on skin. More particularly, the present invention relates to a device for testing the influence of a medicinal or cosmetic substance on skin, while preventing the contamination of perspiration and adhesive in the medicinal or cosmetic substance to be tested.

Hitherto, several attempts have been made to provide a device for testing the influence of a medicinal or cosmetic substance on skin. For example, a piece of porous sheet which is impregnated with or carries thereon a medicinal or cosmetic substance is adhered to an adhesive tape, or a piece of the porous sheet covered with a perforated thin plastic resin film is adhered to an adhesive tape. However, in the above-mentioned types of testing devices, the medicinal or cosmetic substance is contaminated with a portion of the adhesive agent on the adhesive tape, and therefore, the influence on the skin of the adhesive agent is added to the influence of the medicinal or cosmetic substance to be tested. Also, in the above-mentioned types of testing device, it is impossible to prevent the contamination of perspiration in the medicinal or cosmetic substance to be tested.

In another type of testing device, a liquid-non permeable thin film, for example, aluminium foil, is adhered to an adhesive covering sheet, a porous sheet is adhered to the thin film with an adhesive agent, and a medicinal or cosmetic substance to be tested is contained in or carried on the porous sheet. Even with this type of testing device, it was not possible to prevent the contamination of the adhesive agent in the medicinal or cosmetic substance to be tested during the testing operation. Also, the perspiration generated on the skin flows into the porous sheet along the liquid-non permeable thin sheet surface.

In order to eliminate the contamination of the medicinal or cosmetic substance to be tested by the perspiration and the adhesive agent, a tray made of a liquid-non permeable material, for example, aluminium is adhered at its bottom lower surface onto an adhesive covering sheet, and a medicinal or cosmetic substance is contained in the tray. When this type of testing device is fixed on the skin, the inside space of the tray containing the medicinal or cosmetic substance to be tested is sealed by bringing the top end of the peripheral side wall of the tray into contact with the skin. Therefore, contamination of the medicinal or cosmetic substance to be tested in the inside space of the tray by the adhesive agent on the adhesive covering sheet and perspiration generated on the skin can be prevented. However, the adhesive covering sheet is brought into contact with a part of the skin around a part of the skin covered with the tray. That is, the part of the skin adhered to the adhesive covering sheet is very close to the part of the skin covered by the tray. Therefore, if both the adhesive agent of the adhesive covering sheet and the medicinal or cosmetic substance contained in the tray have an influence on the skin, it may be very difficult to distinguish the two influences from each other.

An object of the present invention is to provide a device for testing the influence of a medicinal or cosmetic substance on skin while preventing the contamination of the medicinal or cosmetic substance with perspiration and adhesive agent.

Another object of the present invention is to provide a device for testing the influence of a medicinal or cosmetic substance on skin, the device being capable of detecting the influence of the medicinal or cosmetic substance independently from the influence, on the skin, of another substance, for example, an adhesive agent.

In the present invention, the device for testing the influence of a medicinal or cosmetic substance on skin, comprises:

a tray having a bottom, a periphery side wall extending from the bottom, by which bottom and side wall an inside space for containing a medicinal or cosmetic substance to be tested is defined, and an annular sealing member laterally extending from the top end of the side wall;

a porous protecting sheet having at least one hole in which the tray is contained, and;

a covering sheet having an adhesive surface onto which the lower surface of the bottom of the tray and a surface of the porous protecting sheet are adhered.

The features and advantages of the present invention will be apparent to persons aquainted with this type of testing device upon reading the following description with reference to the accompanying drawings, in which.

Figure 5:
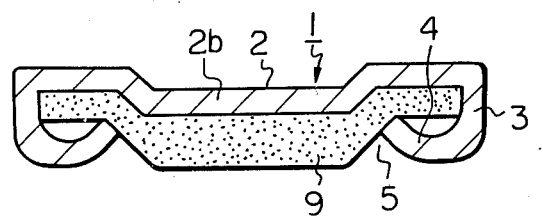
Figure 6:
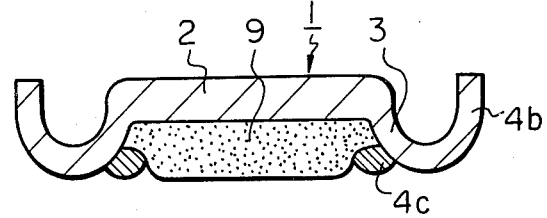
Figure 7:
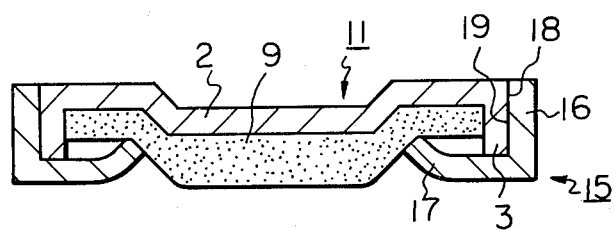
Figure 8:
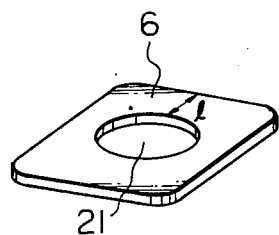
Figure 9:
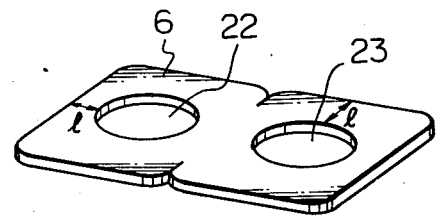

FIGS. 5 through 7 respectively show a cross-sectional view of another embodiment of the tray usable for the present invention, and;

FIGS. 8 and 9 are an explanatory view of an embodiment of a protecting sheet usable for the present invention, respectively.

Figure 1:
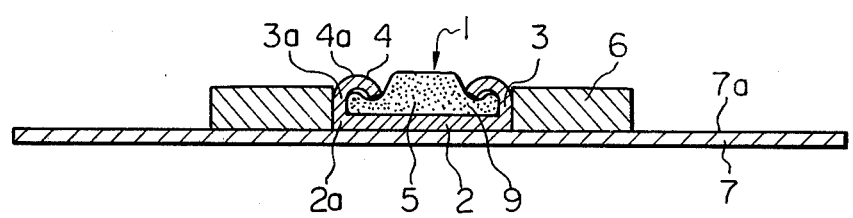
FIG. 1 is an explanatory cross-sectional view of an embodiment of the device of the present invention.

Referring to FIG. 1, a tray 1 has a bottom 2, a periphery side wall 3 and an annular sealing member 4. The side wall 3 extends upward from a peripheral edge 2a of the bottom 2. The annular sealing member 4 extends laterally from a top end 3a of the side wall 3. An inside space 5 of the tray 1 is defined by the bottom 2 and the periphery side wall 3.

A porous protecting sheet 6 has a hole in which the tray 1 is contained. That is, the tray 1 is surrounded by the porous protecting sheet 6.

The lower surface of the bottom 2 of the tray is adhered to a center portion of an adhesive surface 7a of a covering sheet 7. Also, the lower surface of the protecting sheet is adhered to the adhesive surface 7a of the covering sheet so as to surround the tray 1.

The inside space 5 can contain therein a medicinal or cosmetic substance to be tested. The medicinal or cosmetic substance may be contained in or carried on a porous sheet.

When a porous sheet 9 containing therein or carrying thereon the medicinal or cosmetic substance is placed in the inside space 5 of the tray 1 in FIG. 1, the peripheral edge portion of the porous sheet can be caught between the bottom 2 and the sealing member 4 which extends from the top end 3a of the side wall 3 toward the inside space 5 of the tray 1. Therefore, even when the tray is turned over, the porous sheet containing therein or carrying thereon the medicinal or cosmetic substance can be maintained in the inside space 5 of the tray 1.

Figure 2:
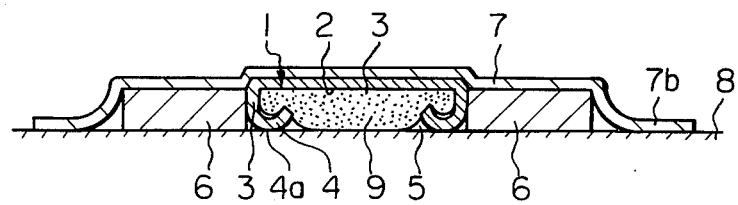
FIG. 2 is an explanatory cross-sectional view of the device shown in FIG. 1 when fixed to the skin.

The testing device shown in FIG. 1, having the porous sheet 9 containing therein or carrying thereon the medicinal or cosmetic substance, can be fixed onto human or animal skin in the manner, for example, shown in FIG. 2. Referring to FIG. 2, the porous sheet 9 containing therein or carrying thereon the medicinal or cosmetic substance to be tested is brought into contact with a predetermined portion of skin 8. A portion of the skin 8 around the portion of the skin contacting the porous sheet 9 is covered by the protecting sheet 6, and a peripheral edge portion 7b of the covering sheet 7 is adhered to a portion of the skin 8 around the portion of the skin covered by the protecting sheet 6, so as to fix the testing device onto the skin 8. As FIG. 2 clearly shows, the portion of the skin contacting the porous sheet 9 is spaced from the portion of the skin adhering to the peripheral edge portion 7b of the covering sheet 7 through the protecting sheet 6. Therefore, the influence of the medicinal or cosmetic substance on the predetermined portion of the skin can be distinguished from the influence of the adhesive agent of the covering sheet on the other portion of the skin.

Referring to FIG. 2, the sealing member 4 has an arc-shaped cross-sectional profile. Therefore, a curved outer surface 4a of the sealing member 4 can contact the skin over a relatively large contact area so as to completely seal the inside space 5 of the tray 1. The large contact area results in no injury to the skin.

The porous sheet for containing therein or carrying thereon the medicinal or cosmetic substance, may be made of paper; cotton mass; a woven, knitted or non-woven fabric; a spongy plastic resin sheet, for example, a spongy polyvinyl chloride sheet or a spongy polyvinyl butyrol sheet; or a foamed plastic resin sheet, for example, a foamed polyurethane sheet or a foamed polystyrene sheet.

The tray may be made of a material which is non-permeable for liquid; for example, a metal, such as aluminium, stainless steel and chromium-plated copper, or a synthetic resin such as polyethylene terephthalate, polyvinyl chloride, polypropylene, polyethylene or polystyrene. The sealing member of the tray may laterally extend from the top end of the side wall of the tray toward the inside space of the tray as shown in FIGS. 1, 2 and 3.

Figure 3:
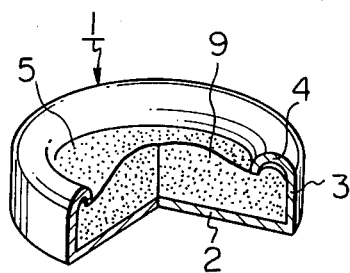
FIG. 3 is a partial cross-sectional view of an embodiment of the tray usable for the present invention.

Referring to FIG. 3, the bottom 2, the side wall 3 and the annular sealing member 4 are connected to each other to form one body of the tray 1, and a porous sheet 9 containing therein or carrying thereon the medicinal or cosmetic substance is placed within the inside space 5 of the tray 1. The peripheral edge portion of the porous sheet 9 is inserted and caught between the bottom 2 and the sealing member 4. Therefore, even when the tray 1 is turned over, the porous sheet 9 can be maintained in the inside space 5 of the tray 1.

Figure 4:
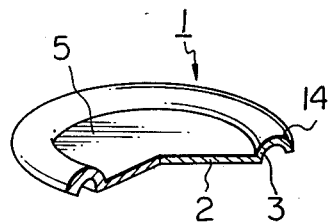
FIG. 4 is a partial cross-sectional view of another embodiment of the tray usable for the present invention.

The annular sealing member may extend from the top end of the side wall toward the outside of the tray. Referring to FIG. 4, the annular sealing member 14, having an arc-shaped cross-sectional profile, extends from the side wall 3 toward the outside of the tray 1. This type of tray can be used when the medicinal or cosmetic substance can be easily fixed to the bottom of the tray or when the tray can be fixed to the skin without turning the tray over.

The bottom of the tray may be flat-surfaced or rough surfaced. Furthermore, a portion of the bottom of the tray may protrude toward the inside space of the tray. Referring to FIG. 5, a center portion 2b of the bottom 2 protrudes toward the inside space of the tray 1. This type of tray is effective for firmly maintaining the porous sheet 9 within the inside space 5 of the tray 1 by the gripping of the peripheral edge portion of the porous sheet 9 between the sealing member 4 and the protruded bottom portion 2b, and is also effective for definitely carrying out the contact of the porous sheet with the skin.

The sealing member of the tray may extend toward both the inside and the outside of the tray. Referring to FIG. 6, an outside annular sealing member 4b extends from the side wall 3 toward the outside of the tray 1 and an inside annular sealing member 4c extends from the side wall 3 toward the inside of the tray. The outside sealing member 4b is effective for completely sealing the inside space of the tray and the inside sealing member 4c is effective for supporting the porous sheet within the tray.

The annular sealing member may be separable from the tray. Referring to FIG. 7, a tray 11 composed of a bottom 2 and a periphery side wall 3 is engaged with an annular sealing device 15 composed of a periphery side wall 16 and a sealing member 17. The sealing device 15 may be separable from the periphery side wall 3 of the tray 11. Otherwise, the outside surface 18 of the side wall 3 of the tray 1 may be bonded to the inside surface 19 of the side wall 16 of the sealing device 15 with an adhesive agent or rivets.

The tray is not limited to a special shape. However, it is preferable that the tray have a circular or oval horizontal cross-sectional profile. Also, the tray is not limited to a special size. However, it is preferable that when the tray has a circular horizontal cross-sectional profile, the inside diameter of the circular tray be in a range of from 3 to 20 mm, and; when the tray has a oval cross-sectional profile, the major axis of the oval tray be in a range of from 5 to 25 mm and the minor axis of the oval tray be in a range of from 3 to 20 mm. Furthermore, the tray is not limited to a special thickness. However, the preferable thickness of the tray is in a range of from 0.1 to 2 mm.

The porous protecting sheet is used for protecting a portion of the skin around the portion of the skin with which the medicinal or cosmetic substance is brought into contact. Referring to FIG. 2, a protecting sheet 6 has a hole 21 in which a tray is contained. The protecting sheet 6 is made of a liquid absorbing porous material, permeable for gas and liquid. For example: paper; cotton mass; woven, knitted or non-woven fabric; a spongy plastic resin sheet, such as a spongy polyvinyl chloride sheet or a spongy polyvinyl butyral; or a foamed plastic resin sheet, such as a foamed polyurethane sheet or foamed polystyrene sheet.

The protecting sheet may be provided with two or more separate holes, each of which may contain one tray. Referring to FIG. 9, a protecting sheet 6 has two holes 22 and 23 each of which contains one tray. The shape and size of the hole in the protecting sheet is adjusted so as to be adapted to contain therein the tray. However, it is preferable that the protecting sheet have a thickness in a range of from 0.1 to 2 mm. The protecting sheet is effective for absorbing the perspiration generated on the skin and preventing the contamination of the medicinal or cosmetic substance by the perspiration. Also, the protecting sheet can absorb a portion of the medicinal or cosmetic substance to be tested, which is leaked from the inside space of the tray, and can protect the portion of the skin covered by the protecting sheet from the influence of the leaked medicinal or cosmetic substance.

Referring to FIGS. 8 and 9, it is preferable that the distance 1 between the inside peripheral surface defining the hole of the protecting sheet and the outside peripheral edge of the protecting sheet be at a minimum 1 mm, more preferably, from 2 to 10 mm. Also, when the protecting sheet has two or more holes, the distance between the inside peripheral surfaces defining the holes is at a minimum 1 mm, more preferably, from 2 to 50 mm. That is, it is preferable that the tray be surrounded with a minimum of 1 mm, more preferably, 2 to 30 mm, of the protecting sheet.

The covering sheet has an area larger than that of the protecting sheet including the hole or holes formed therein. That is, the peripheral edge portion of the covering sheet must extend outward from the outside peripheral edge of the protecting sheet adhered thereto. The peripheral edge portion of the covering sheet can adhere to the portion of the skin around the portion of the skin covered by the protecting sheet so as to fix the testing device to the skin.

The covering sheet may be made of paper; woven, knitted or non-woven fabric; or plastic resin film, for example, a film of polyethylene, polypropylene, polyethylene terephthalate, polyvinyl chloride, regenerated cellulose, cellulose derivative, for instance, cellulose acetate. The covering sheet has an adhesive surface coated with a pressure-sensitive adhesive agent, for example, a natural rubber, synthetic rubber, acrylic copolymer or vinyl acetate copolymer. It is preferable that the adhesive agent have no influence on human or animal skin.

The medicinal or cosmetic substance to be tested may be in the form of a liquid, solid, paste, powder or semi-solid. When the medicinal or cosmetic substance is a liquid, it is preferable that the substance be absorbed in a porous material. When the substance is a paste or viscous liquid, it is preferable that the substance be coated on a surface of the porous material. When the substance is a solid, powder or semi-solid, the inside space of the tray may be filled with the solid, powdered or semi-solid substance, so that the substance filled in the tray can come into the direct contact with the skin.

The testing device of the present invention is effective for accurately testing the influence of a medicinal or cosmetic substance on human or animal skin.

What we claim is:

1. A device for testing the influence of a medicinal or cosmetic substance on skin, comprising:
   a tray having a bottom, a periphery side wall extending from the bottom, by which bottom and side wall an inside space for containing a medicinal or cosmetic substance to be tested is defined, and an annular sealing member laterally extending from the top end of the side wall;
   a porous protecting sheet having at least one hole formed therein, in which hole the tray is contained, and;
   a covering sheet having an adhesive surface onto which the outside surface of the bottom of the tray and a lower surface of the protecting sheet are adhered.

2. A device as claimed in claim 1, wherein the tray is made of a metal or synthetic resin.

3. A device as claimed in claim 1, wherein the porous protecting sheet is made of paper, cotton mass, a woven, knitted or non-woven fabric, a spongy plastic resin sheet or a foamed plastic resin sheet.

4. A device as claimed in claim 1, wherein the annular sealing member extends toward the inside space of the tray.

5. A device as claimed in claim 1, wherein the annular sealing member extends toward the outside of the tray.

6. A device as claimed in claim 1, wherein the annular sealing member has an arc-shaped cross-sectional profile.

7. A device as claimed in claim 1, wherein the medicinal or cosmetic substance to be tested is contained in a porous sheet placed in the inside space of the tray.

8. A device as claimed in claim 7, wherein the porous sheet containing the medicinal or cosmetic substance is made of paper, cotton mass, a woven, knitted or non-woven fabric, a spongy plastic resin sheet or a foamed plastic resin sheet.

9. A device as claimed in claim 1, wherein the distance between the inside peripheral surface defining the hole of the porous protecting sheet and an outside periphery edge of the protecting sheet is at minimum 1 mm.

10. A device as claimed in claim 1, wherein a portion of the bottom of the tray protrudes toward the inside space of the tray.

* * * * *